United States Patent
Zhang et al.

(10) Patent No.: US 9,501,626 B2
(45) Date of Patent: Nov. 22, 2016

(54) SMART AUTOMATED PILL DISPENSER

(71) Applicants: Dafang Zhang, Boston, MA (US); Ashwin Nathan, Newtown Square, PA (US); Allen Cheng, Cambridge, MA (US); Eli Cohen, Somerville, MA (US)

(72) Inventors: Dafang Zhang, Boston, MA (US); Ashwin Nathan, Newtown Square, PA (US); Allen Cheng, Cambridge, MA (US); Eli Cohen, Somerville, MA (US)

( * ) Notice: Subject to any disclaimer, the term of this patent is extended or adjusted under 35 U.S.C. 154(b) by 378 days.

(21) Appl. No.: 13/904,057

(22) Filed: May 29, 2013

(65) Prior Publication Data

US 2014/0358278 A1 Dec. 4, 2014

(51) Int. Cl.
 G07F 17/00 (2006.01)
 G06F 19/00 (2011.01)

(52) U.S. Cl.
 CPC ....... *G06F 19/3462* (2013.01); *G07F 17/0092* (2013.01)

(58) Field of Classification Search
 CPC .................. G07F 17/0092; G06F 19/3462
 USPC .................................................. 700/240, 242
 See application file for complete search history.

(56) References Cited

U.S. PATENT DOCUMENTS

| | | |
|---|---|---|
| 4,572,403 A | 2/1986 | Benaroya |
| 4,573,606 A | 3/1986 | Lewis et al. |
| 4,674,651 A | 6/1987 | Scidmore et al. |
| 4,838,453 A | 6/1989 | Luckstead |
| 5,044,516 A | 9/1991 | Hoar |
| 5,176,285 A | 1/1993 | Shaw |
| 5,240,324 A * | 8/1993 | Phillips et al. ............... 366/132 |
| 5,392,952 A | 2/1995 | Bowden |
| 5,472,113 A | 12/1995 | Shaw |
| 5,564,593 A | 10/1996 | East, Sr. |
| 5,609,268 A | 3/1997 | Shaw |
| 5,884,806 A * | 3/1999 | Boyer et al. ..................... 221/75 |
| 6,068,158 A | 5/2000 | Chabout |
| 6,510,962 B1 | 1/2003 | Lim |
| 6,702,146 B2 | 3/2004 | Varis |
| 7,048,141 B2 | 5/2006 | Abdulhay et al. |
| 7,210,598 B2 * | 5/2007 | Gerold et ...................... 221/123 |
| 7,213,721 B2 | 5/2007 | Abdulhay et al. |
| 7,624,894 B2 * | 12/2009 | Gerold et al. ................ 221/124 |
| 7,711,449 B2 | 5/2010 | Abdulhay et al. |

(Continued)

OTHER PUBLICATIONS

Fischer, M.A., et al. Primary medication non-adherence: analysis of 195,930 electronic prescriptions. Journal of general internal medicine 25, 284-290 (2010).

(Continued)

*Primary Examiner* — Patrick Cicchino
(74) *Attorney, Agent, or Firm* — Lambert & Associates; Gary E. Lambert; David J. Connaughton, Jr.

(57) ABSTRACT

Dispensing machine. The machine includes a number of silos for the storage of smaller objects and a mechanism for dispensing the stored objects into a central receptacle at a designated time or frequency in a combinatorial manner, regardless of the size, shape, or other physical characteristics of the pill to be dispensed. Major components of the device include a number of silos for storing objects of dispersal, a user input interface, a circuit board, an actuator, a central receptacle, a sensor, a storage receptacle, and an alarm. It is preferred that the designated time or frequency for dispersal from each silo is set by a user or a third-party. It is preferred that the machine further includes a capability for wireless connectivity to an intranet or an internet and a mechanism for monitoring access to the central receptacle and for outputting feedback to a user or a third-party.

20 Claims, 4 Drawing Sheets

(56) References Cited

U.S. PATENT DOCUMENTS

| | | | | |
|---|---|---|---|---|
| 7,853,355 | B1* | 12/2010 | Willemse et al. | 700/243 |
| 8,622,196 | B1* | 1/2014 | Lapointe | 198/383 |
| 8,655,486 | B2* | 2/2014 | Sanders et al. | 700/242 |
| 9,072,652 | B1* | 7/2015 | Balasubramanian et al. | |
| 2011/0301747 | A1* | 12/2011 | Chambers | 700/231 |
| 2011/0313567 | A1* | 12/2011 | Willemse et al. | 700/242 |
| 2014/0138398 | A1* | 5/2014 | Daniels et al. | 221/1 |

OTHER PUBLICATIONS

Glombiewski, J.A., Nestoriuc, Y., Rief, W., Glaesmer, H. & Braehler, E. Medication adherence in the general population. PloS one 7, e50537 (2012).

Boskovic, J., Leppee, M., Culig, J. & Eric, M. Patient self-reported adherence for the most common chronic medication therapy. Scandinavian journal of public health (2013).

Cohen, C., Davis, K. & Meyers, J. Association of partial adherence (PA) to antiretroviral therapy with hospitalizations and healthcare costs in an HIV population. Journal of the International AIDS Society 15 Suppl 4, 18060 (2012).

Sokol, M.C., McGuigan, K.A., Verbrugge, R.R. & Epstein, R.S. Impact of medication adherence on hospitalization risk and healthcare cost. Medical care 43, 521-530 (2005).

Gellad, W.F., Grenard, J.L. & Marcum, Z.A. A systematic review of barriers to medication adherence in the elderly: looking beyond cost and regimen complexity. The American journal of geriatric pharmacotherapy 9, 11-23 (2011).

Ownby, R.L. Medication adherence and cognition. Medical, personal and economic factors influence level of adherence in older adults. Geriatrics 61, 30-35 (2006).

Foundation, K.F. Prescription Drug Trends. 3057-08(2010).

Haynes, R.B., Ackloo, E., Sahota, N., McDonald, H.P. & Yao, X. Interventions for enhancing medication adherence. Cochrane Database Syst Rev, CD000011 (2008).

Osterberg, L. & Blaschke, T. Adherence to medication. The New England journal of medicine 353, 487-497 (2005).

* cited by examiner

SMART AUTOMATED PILL DISPENSER

FIELD OF THE INVENTION

This invention relates to dispensers for the automated organization and dispersal of small objects at a designated time or frequency, and more particularly to such a machine that organizes and dispenses pills or medications in accordance to a designated time or frequency.

BACKGROUND OF THE INVENTION

Medication non-adherence has become one of the nation's biggest public health burdens, costing over $170 billion annually. 50-75% of patients are estimated to be non-adherent, particularly in common chronic diseases such as hypertension, hyperlipidemia, and diabetes. Non-adherence leads to poor management of chronic disease, significantly higher death rates, and weakening of the physician-patient relationship. Causes of non-adherence include complicated treatment regimens, inconvenience, cognitive ability, manual dexterity, and forgetfulness, problems exacerbated by age. The average number of prescriptions per capita is 12.6, not including supplements. Patients have increasingly more difficulty with adherence to a medication regimen as the number of prescribed medications increases and as the dosing frequency varies.

Presently available solutions to non-adherence address some patient frictions but prove either ineffective or impractical at scale. Simple, singular interventions such as alarms, monitoring, and follow-up calls are marginally effective. The simple pillbox allows patients to pre-organize medications into time slots; however, it requires high motivation, cognitive function, and manual dexterity to preload the pillbox reliably without error. Furthermore, most models do not alert the patient to take the medication at the necessary time. The demand for a device that automatically dispenses pills at a designated time is evidenced by the prior art literature, which include U.S. Pat. No. 4,572,403 to Ben-aroya, U.S. Pat. No. 4,573,606 to Lewis, U.S. Pat. No. 4,674,651 to Scidmore, U.S. Pat. No. 4,838,453 to Luckstead, U.S. Pat. No. 5,044,516 to Hoar, U.S. Pat. No. 5,176,285 to Shaw, U.S. Pat. No. 5,392,952 to Bowden, U.S. Pat. No. 5,472,113 to Shaw, U.S. Pat. No. 5,564,593 to East, U.S. Pat. No. 5,609,268 to Shaw, U.S. Pat. No. 6,068,158 to Chabout, U.S. Pat. No. 6,510,962 to Lim, and U.S. Pat. No. 6,702,146 to Varis. However, while prior art pill dispensing machines and systems illustrate the capacity to automatically dispense pills, these machines and systems rely on manual loading of pill storage compartments to include the precise set of pills to be dispensed at each dispersal time point. The process of manually loading pill storage compartments is challenging for users with limited manual dexterity. In the case that pills in loaded pill storage compartments need to be exchanged, each pill storage compartment needs to be manually reloaded and the contents of each pill storage compartment manually resorted. Such limitations of prior art pill dispensing machines and systems create behavioral disincentives to user adoption.

Abdulhay in U.S. Pat. No. 7,048,141, U.S. Pat. No. 7,213,721, and U.S. Pat. No. 7,711,449 attempts to overcome these deficiencies by dispensing pills in a combinatorial manner from separate silos; however, Abdulhay's means of dispersal requires separate built-in funnels to accommodate different pill sizes. Given the ever-growing variety of pill sizes and shapes, such a finite, limited approach to combinatorial pill dispersal is still yet inadequate.

It is an object of the present invention to provide a pill dispersal system that overcomes the disadvantages of prior art medication organizing and dispensing devices. A specific object is to provide a pill dispensing that offers a centralized system of pill organization and dispersal; a capacity for dynamic, modular alteration of pills; a user-friendly interface; an alert system; and a system for behavioral feedback.

SUMMARY OF THE INVENTION

The machine according to the invention includes a number of silos for the storage of smaller objects and a mechanism for dispensing the stored objects into a central receptacle at a designated time or frequency in a combinatorial manner. In such a mechanism, the objects of dispersal are stored in respective compartments until the time of dispersal, at which time a programmed combination of objects are dispensed to the central receptacle. In a preferred embodiment, the stored objects are pills or medications.

The machine according to the invention includes a user input interface, a circuit board, and an actuator. It is preferred that a user input interface provides an input signal through a circuit board to an actuator. An actuator acts to dispense one or more object at a time from each silo until the designated number of object or objects from the designated silo or silos are dispensed at the designated time or frequency. It is preferred that the designated time or frequency for dispersal from each silo is set by the user through the user input interface or through a third-party remotely.

It is preferred that the machine disclosed herein includes a mechanism of alerting a user when a dispersal event has taken place. In a preferred embodiment, an alert may be an acoustic or a visual stimulus. In a preferred embodiment, an alert may be a telephone call or an electronic message such as an e-mail, a text message, a multimedia message, or the like.

It is preferred that the machine disclosed herein includes a mechanism of moving previously dispensed objects in the central receptacle to a separate storage receptacle prior to additional dispersal.

It is preferred that the machine disclosed herein includes a mechanism of dispensing the next queue of objects when a third-party designates such an action through the user input interface.

It is preferred that the machine disclosed herein includes a mechanism of alerting a user or a third-party when contents of a silo or silos are empty or low, as it may prompt a user to refill a silo or silos.

It is preferred that the machine disclosed herein includes a mechanism of emptying a silo if the contents of the silo are no longer deemed necessary, when a third-party designates such an action through the user input interface.

It is preferred that the machine disclosed herein includes a mechanism for monitoring access to the central receptacle, for storing data in regards to access to the central receptacle, and for outputting stored data to a user or a third party.

It is preferred that the machine disclosed herein includes a capability for wireless connectivity to an intranet or an internet, and that input or output of the machine may be wirelessly modulated.

In a preferred embodiment, a user is a patient, family member of a patient, or caregiver. In a preferred embodiment, a third-party is a family member of a patient, caregiver, or healthcare professional.

REFERENCE NUMERALS FIGS. 1 TO 4

Figure 1:
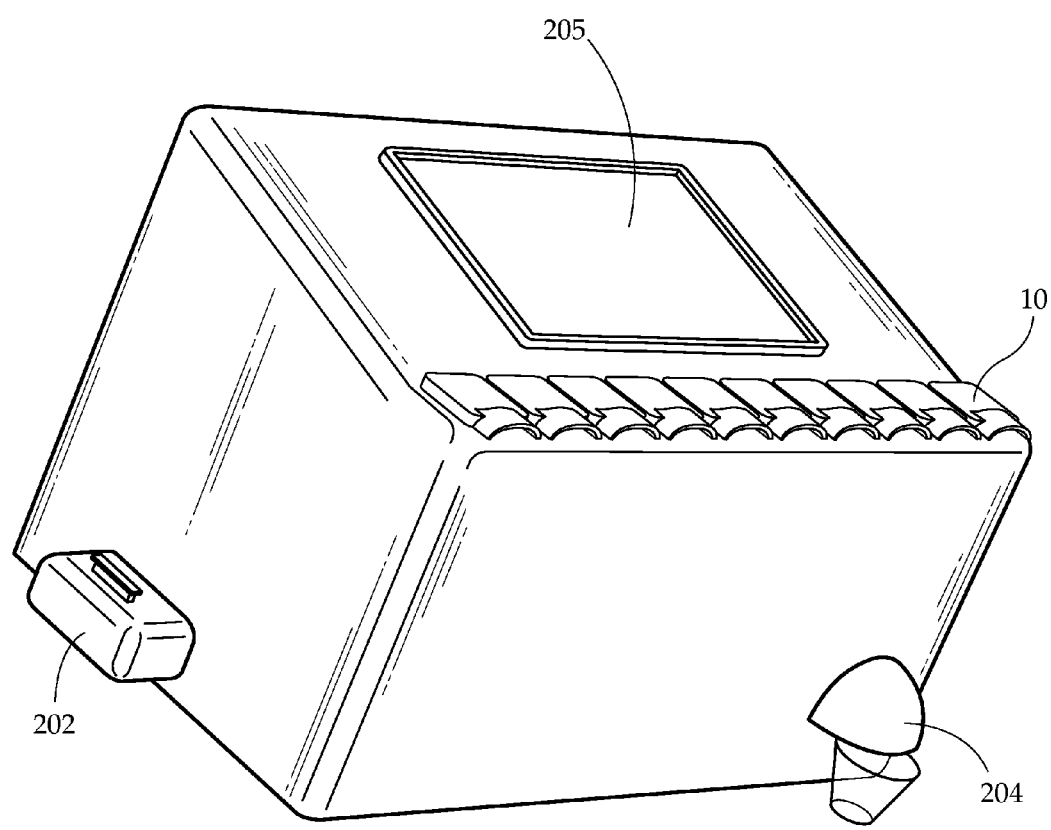
FIG. 1 is a perspective illustration of the exterior of a preferred embodiment of the machine disclosed herein.

10 hopper lid
11 hopper
12 auger
13 cylindrical encasement for auger
14 custom slotted screw head of auger
15 axial shaft of rotary actuator
16 linear track for engagement with auger
17 linear actuator for engagement with auger
18 rotary actuator for auger
19 infrared pill sensor and counter
20 pill sorting receptacle
21 rotary actuator for pill sorting receptacle
22 error chute
23 connector
24 inferior linear guide rail for drive motor
25 superior linear guide rail for drive motor
26 threaded track for drive motor
27 left wall of exterior encasement
200 drive motor for actuator mechanism
201 right wall of exterior encasement
202 error receptacle
203 dispersal chute
204 dispersal receptacle
205 user interface screen

DESCRIPTION OF THE PREFERRED EMBODIMENT

A perspective front exterior view of a preferred embodiment of the presently disclosed invention is shown in FIG. 1. FIG. 1 shows important exterior components of the machine, including a number of hopper lids 10, a pill dispersal receptacle 204, an error receptacle 202, and a user interface screen 205. The hoppers depicted serve as silos or compartments for pill storage. The number of hoppers included on the machine may include 1, 2, 3, 4, 5, 6, 7, 8, 9, 10, 11, 12, 13, 14, 15, or more than 15.

Figure 2:
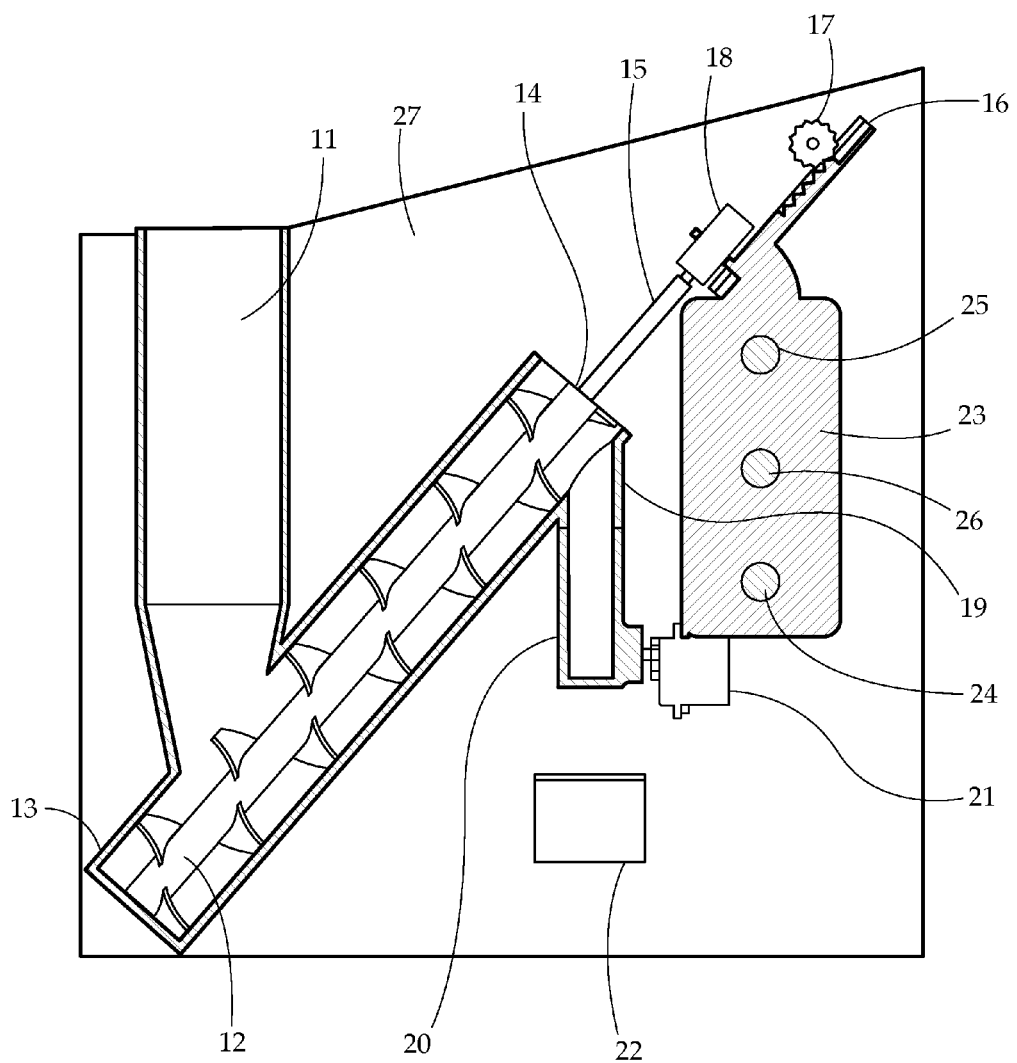
FIG. 2 is a cross-sectional depiction of the actuation mechanism of the machine of FIG. 1.

A cross-sectional depiction of the actuation mechanism of the machine of FIG. 1 is shown in FIG. 2. As shown, directly underneath each hopper lid 10 is a hopper 11 capable of pill storage. Each hopper 11 is in directly connection with an auger 12 encased by a cylindrical encasement 13. At the superior tip of the root of the auger is a custom slotted screw head 14 capable of engaging with the axial shaft 15 of a rotary actuator 18. Engagement of axial shaft 15 with screw head 14 is enabled by a linear actuator 17 by means of a linear track 16. Pills are able to be propelled from storage in the hopper to dispersal by the actuation mechanism depicted.

When a pill is propelled to dispersal by the auger system, it falls via gravity through an infrared pill sensor and counter 19 into a pill sorting receptacle 20. The pill sensor and counter 19 uses infrared light at each dispersal event to count the exact number of pills dispensed. If the number of pills counted is equal to the schedule number to be dispensed from that particular hopper, henceforth known as a successful count event, the pill sorting receptacle 20 is ultimately rotated clockwise by a rotatory actuator for the pill sorting receptacle 21 such that the dispensed pill(s) falls into a dispersal chute 203. The dispersal chute 203 seen internally is connected to a dispersal receptacle 204 seen externally. If the number of pills counted is not equal to the schedule number to be dispensed from that particular hopper, henceforth known as a failed count event, the pill sorting receptacle 20 is ultimately rotated counterclockwise by a rotatory actuator 21 such that the dispensed pill(s) falls into an error chute 22. FIG. 2 clearly depicts that the actuators that drive the auger are in physical connection with the actuator that rotates the pill sorting receptacle through connector 23.

Figure 3:
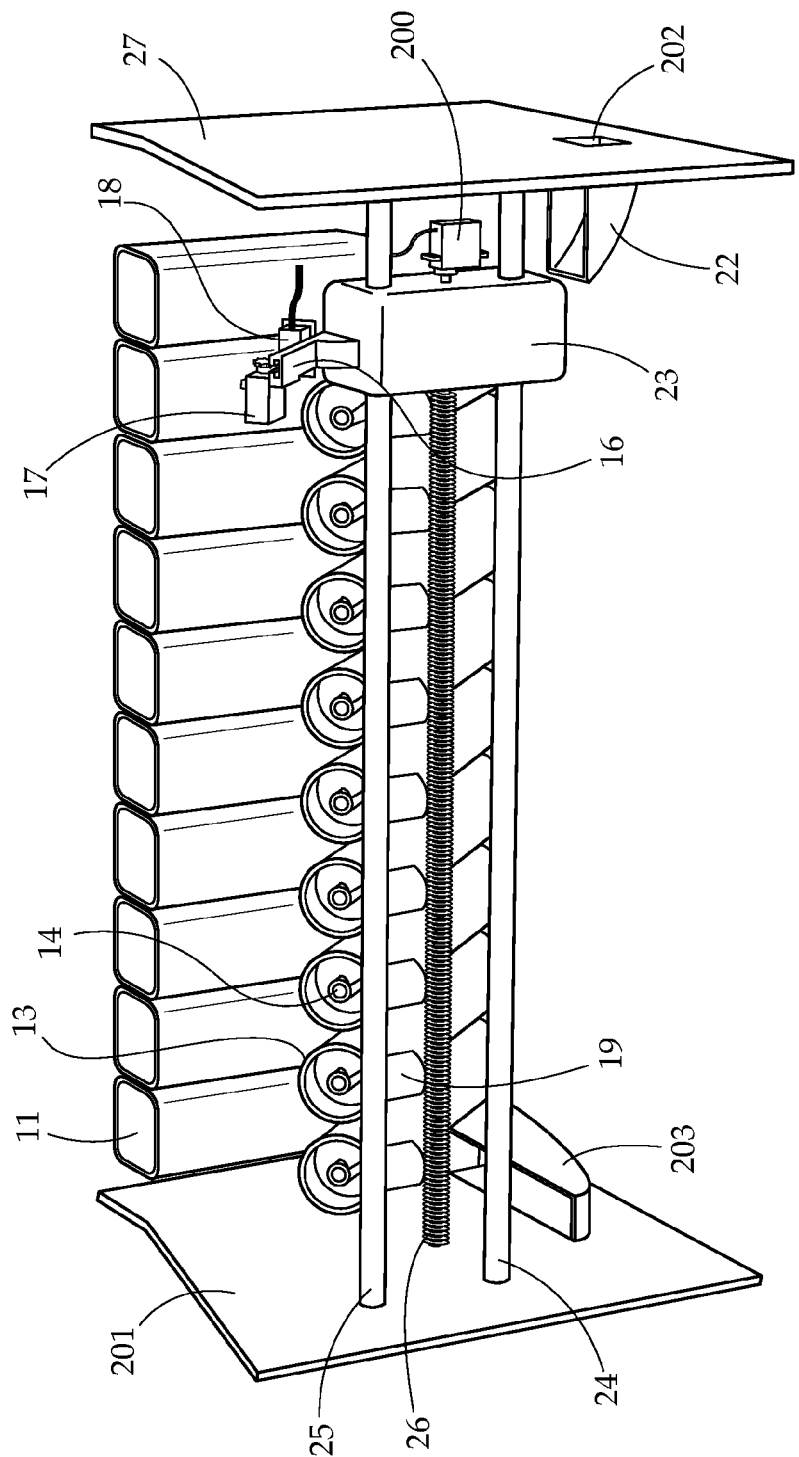
FIG. 3 is a right oblique perspective illustration of the rear of the machine of FIG. 1.

A right oblique perspective illustration of the rear of the machine of FIG. 1 is shown in FIG. 3. Again is seen a series of hoppers 11—herein 10 hoppers arranged linearly are depicted—connected to an auger-driven dispersal system. Augers are encased within cylindrical encasements 13. At the superior tip of each auger is a custom slotted screw head 14, well-depicted at this angle. Again is seen the linear track 16 and linear actuator 17 for engagement with each auger as well as the rotatory actuator for each auger 18. Again is seen the infrared pill sensor and counter 19, one for each hopper-auger combination. The rotatory actuator for the pill sorting receptacle 21 is visualized. In this right oblique perspective view, it is apparent that connector 23 is mobile and able to be driven by a drive motor 200. The path of connector 23 is confined by a threaded track 26, and further confined by two linear guide rails, one inferior 24 and one superior 25. The movement of connector 23 allows the pill sorting receptacle 20 to sit directly underneath any infrared pill sensor and counter 19, so that pills dispensed from any hopper-auger combination can be collected and sorted by one pill sorting receptacle 20. Moreover, with each successful count event, the drive motor 200 drives the connector 23, and therefore the pill sorting receptacle 20 by virtue of their physical connection, towards the right wall 201, and the pill(s) are dropped via gravity into the dispersal chute 203 by a rotatory actuator for the pill sorting receptacle 21. With each failed count event, the drive motor 200 drives the connector 23, and therefore the pill sorting receptacle 20, towards the left wall 27, and the pill(s) are dropped via gravity into the error chute 22. The dispersal chute 203 seen internally is connected to a dispersal receptacle 204 seen externally. The error chute 22 seen internally is connected to an error receptacle 202 seen externally.

Figure 4:
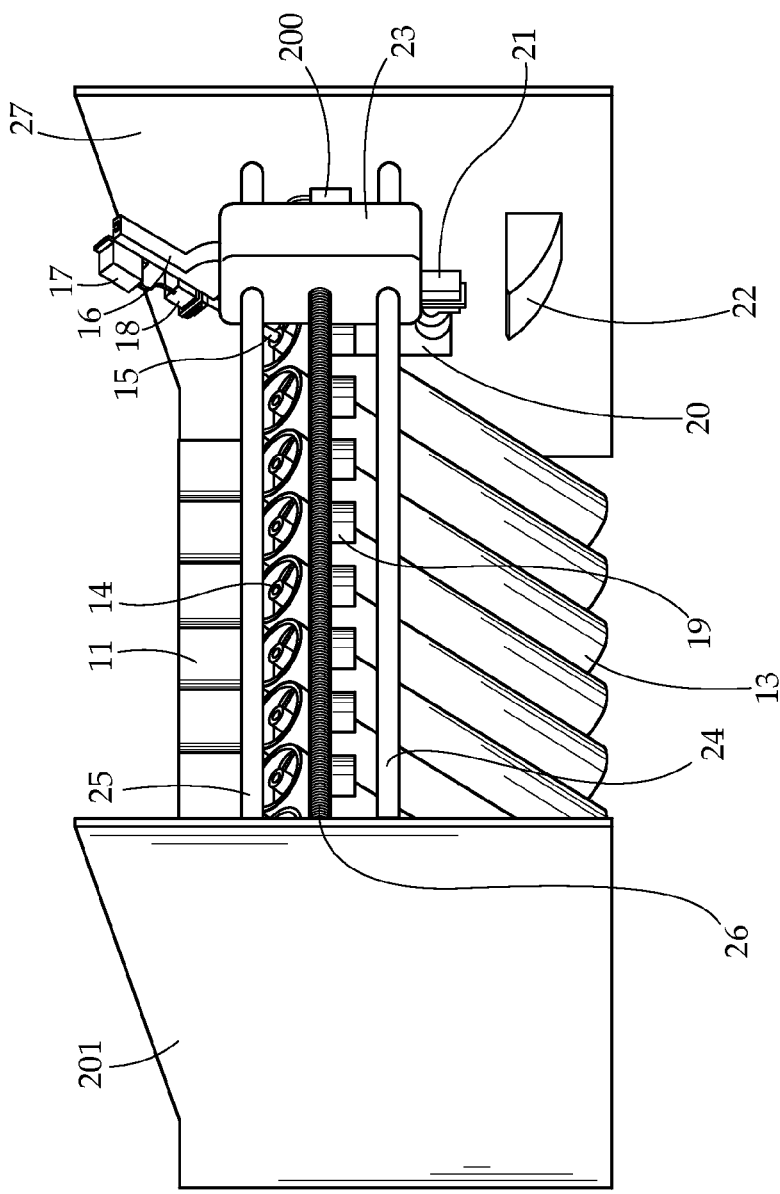
FIG. 4 is a left oblique perspective illustration of the rear of the machine of FIG. 1.

A left oblique perspective illustration of the rear of the machine of FIG. 1 is shown in FIG. 4. Well-depicted in this angle is the intricate mating of the axial shaft 15 and the screw head of the auger tip 14 as well as the apposition of the pill sensor and counter 19 with the pill sorting receptacle 20. The superior aspect of the pill sorting receptacle 20 is rounded off such that it is able to rotate unhindered.

Components of the preferred embodiment of the machine disclosed herein have been omitted from the drawings for the sake of clarity. These components include the power source, battery, circuit board, timer, acoustic and visual alarms, wireless and multimedia accessibility devices, a separate storage receptacle for pills not taken from the dispersal receptacle, and the like. Aside from the actuators, circuits, and other hardware, most of the components of the preferred embodiment can be fashion from plastics.

Operation of the Preferred Embodiment

To initially use the preferred embodiment of the machine disclosed herein, the user should first connect the power source to an AC power outlet or recharge or replace the battery as needed. The user should lift each hopper lid 10 and fill each hopper 11 with a specific type of medication pill for the desired number of medications or the maximum number of hoppers available, whichever is lower. Upon turning on the dispensing machine, the user should use the user interface screen 205 to program the dispersal schedule for each hopper in use. In a preferred embodiment, user programming is accomplished through a touchscreen interface 205, but other embodiments may use buttons.

Now, take for example that the user is schedule to receive 1 pill from hopper 1, 2 pills from hopper 2, and 3 pills from hopper 3 at 9 o'clock AM. The machine, shortly prior to 9 o'clock AM, automatically begins the dispersal process, as directed by the internal timer. The drive motor 200 first drives the connector 23 to align with hopper 1. Pills in the hopper 11 collect via gravity within the auger apparatus 12 enclosed in a cylindrical encasement 13. The linear actuator 17 drives the axial shaft 15 on the linear track 16 to engage with the custom slotted screw head of the auger 14. The rotatory actuator 18 then begins to turn the auger, propelling pills in the hopper-auger system up along the turning threads at a rate slow enough such that pills drop out of the auger one by one. As 1 pill is dropped, it is counted by the infrared sensor and counter 19 and falls into the pill sorting receptacle 20, thereby shutting off the rotatory actuator 18 driving the auger. Since a successful count event was detected by the sensor 19, the drive motor 200 drives the connector 23 towards the right wall 201, and the 1 pill is dispensed into the dispersal chute 203 by the rotatory actuator 21 of the pill sorting receptacle. The drive motor 200 then aligns the connector 23 with hopper 2 for the next medication. A similar process ensues for the second medication; however, in this case, the rotatory actuator 18 for the auger is not shut off until 2 pills are counted, at which point the 2 pills will be dropped into the dispersal chute 203. Now, take for example that the drive motor is aligned with hopper 3 and the auger is being driven; however, by happenstance, 4 pills are dropped from the auger instead of 3. The rotatory actuator 18 is again shut off because 3 pills have been dropped. However, because a failed count event has occurred, the drive motor 200 drives the connector 23 towards the left wall 27, and the incorrect number of pills are dispensed into the error chute 22 by the rotatory actuator 21 of the pill sorting receptacle. The drive motor 200 then aligns the connector 23 again with hopper 3 to reattempt dispersal of this medication. Upon a successful count event, the correct number of pills will be dispensed into the dispersal chute 203. At 9 o'clock AM, an acoustic and visual alarm will alert the patient that pills are ready in the dispersal receptacle. The patient should take the dispensed pills and interact with the user interface screen 205 to disable the alarm, indicating pill adherence at that time. A user or a third-party may at any time check the error receptacle to check for pills dropped by error and restock these pills. If a user does not take the pills in the dispersal receptacle prior to the next scheduled dispersal event, the pills are automatically emptied into a separate storage receptacle for missed pills. Users and third-parties have access to the separate storage receptacle to take or restock these pills.

A feature of the preferred embodiment is the ability to dispense the next scheduled set of pills when the user prompts using the user input interface, thereby allowing the user to receive his schedule medications early if the user will be always from the machine at the next scheduled dispersal event.

A feature of the preferred embodiment is an automated system for behavioral feedback. With internet capabilities, the machine disclosed herein is able to continuously upload medication adherence data to be viewed by users and caregivers. This feedback system not only encourages users to adherence to their pill regimens, but also provides caregivers a means of monitoring adherence more closely as needed or desired.

Detailed examples of how a patient might use the present pill dispensing machine are as follows:

Medication Regimen:
Drug A—Twice daily medication
Drug B—Once daily medication, adherence is important
Drug C—Twice daily medication Example of Normal Use:
7:30 AM—Patient wakes up
7:50 AM—Patient eats breakfast in kitchen
8:00 AM—Dispersal of Drug A, Drug B and Drug C; patient is alerted
8:01 AM—Patient addresses machine and stops alarm
8:02 AM—Patient takes medications from dispersal receptacle and consumes them
8:30 AM—Patient leaves home
5:30 PM—Patient returns home
7:30 PM—Patient watches television in living room
8:00 PM—Dispersal of Drug A and Drug C; patient is alerted
8:01 PM—Patient addresses machine and stops alarm
8:02 PM—Patient takes medications from dispersal receptacle and consumes them Example of Non-adherence:
7:30 AM—Patient wakes up
7:50 AM—Patient leaves for work early
8:00 AM—Dispersal of Drug A, Drug B and Drug C; patient is alerted
8:10 AM—Machine automatically stops alarm
8:10 AM—Medications moved to silo for unused pills
8:10 AM—Patient and caregiver notified that morning dose of medication not taken (through email, text messaging, phone call, or the like)
5:30 PM—Patient returns home
7:30 PM—Patient watches television in living room
8:00 PM—Dispersal of Drug A, Drug B, and Drug C (Drug B is dispersed since machine noted it was not taken in AM); patient is alerted
8:01 PM—Patient addresses machine and stops alarm
8:02 PM—Patient takes medications from dispersal receptacle and consumes them Example of Advance Dispensal:
7:30 AM—Patient wakes up
7:50 AM—Patient eats breakfast in kitchen
8:00 AM—Dispersal of Drug A, Drug B and Drug C; patient is alerted
8:01 AM—Patient addresses machine and stops alarm
8:02 AM—Patient takes medications from dispersal receptacle and consumes them
8:03 AM—Patient expects to return home late at night and requests next dose from the machine
8:04 AM—Dispersal of Drug A and Drug C; patient is alerted
8:04 AM—Patient addresses machine and stops alarm
8:04 AM—Patient takes medications from receptacle and places them in storage container for later consumption
8:30 AM—Patient leaves home 8:00 PM—Patient notified it is time to take evening medications that were previously dispensed (through email, text messaging, phone call, or the like)
8:01 PM—Patient takes medications from storage container and consumes them
9:00 PM—Patient returns home The Smart Automated Pill Dispenser offers a centralized system of pill organization and dispersal; a capacity for dynamic, modular alteration of pills; a user-friendly interface; an alert system; and a system for behavioral feedback.

It is recognized that modifications and variations of the present invention will occur to those of ordinary skill in the art and it is intended that all such modifications and variations be included within the scope of the appended claims.

What is claimed is:

1. A device for storage and dispensing of a plurality of small objects comprising:
    a user input interface in electronic communication with a dispensing machine, the user input interface communicating an input signal to the dispensing machine, the input signal providing a count of dispensing a plurality of small objects; and
    the dispensing machine comprising:
        two adjacent storage-auger devices and a connector, each one of the two storage-auger devices comprising:
            a storage container, the storage container defining a substantially hollow interior portion, the hollow interior portion having an inlet and an outlet;
            an auger housing defining an interior chamber, the interior chamber being in communication with the storage container outlet;
            a rotatable auger disposed within the interior chamber of the auger housing constructed and arranged to propel at least one of the plurality of small objects in the interior chamber of the auger housing towards an outlet of the auger housing; and
            a counter in communication with the outlet of the auger housing, the counter configured to count the at least one of the plurality of small objects being dispensed from the outlet of the auger housing into a sorting receptacle;
        the connector being physically connected to the sorting receptacle, the connector and sorting receptacle movable from one storage-auger device to the other storage-auger device such that the at least one of the plurality of small objects dispensed from each one of the storage-auger devices is collected in the sorting receptacle wherein the sorting receptacle is configured to release the plurality of small objects into a dispersal chute.

2. The device for storage and dispensing of a plurality of small objects of claim 1 wherein the rotatable auger is configured to propel the plurality of small objects towards the outlet of the auger housing using an actuator system mounted on one of the connector, the rotatable auger of one of the two storage-auger devices, or the auger housing of one of the two storage-auger devices.

3. The device for storage and dispensing of a plurality of small objects of claim 2 wherein the actuator system comprises:
    a screw head embedded on a distal end of each of the rotatable augers;
    an axial shaft engageable with the screw head using a linear actuator; and
    a rotary actuator propelling the plurality of small objects up along the rotatable auger by providing a rotary motion of the rotatable auger as the axial shaft engages the screw head.

4. The device for storage and dispensing of a plurality of small objects of claim 1 wherein the counter is configured to communicate with the dispensing machine to stop the rotatable auger following a successful count, the successful count being when the plurality of small objects counted by the counter is equal to the plurality of small objects scheduled to be dispensed from the storage-auger device according to the count of the input signal from the user input interface.

5. The device for storage and dispensing of a plurality of small objects of claim 4 wherein the sorting receptacle is configured to release the plurality of small objects into a dispersal chute upon communication to the dispensing machine by the counter of the successful count, the dispersal chute being in communication with a dispersal receptacle where the plurality of small objects are accessible to a user.

6. The device for storage and dispensing of a plurality of small objects of claim 5 further comprising a mechanism of alerting the user when to access the dispersal receptacle, the mechanism of alerting being at least one of an audio alert, visual alert, and a vibrating alert.

7. The device for storage and dispensing of a plurality of small objects of claim 1 wherein the counter is configured to communicate with the dispensing machine to stop the rotatable auger following a failed count, the failed count being when the plurality of small objects counted by the counter is not equal to the plurality of small objects scheduled to be dispensed from the storage-auger device according to the count of the input signal from the user input interface.

8. The device for storage and dispensing of a plurality of small objects of claim 7 wherein the sorting receptacle is configured to release the plurality of small objects into an error chute upon communication to the dispensing machine by the counter of the failed count, the error chute being in communication with an error receptacle where the plurality of small objects are accessible to the user.

9. The device for storage and dispensing of a plurality of small objects of claim 8 further comprising a second mechanism of alerting the user when to access the error receptacle, the second mechanism of alerting being at least one of an audio alert, visual alert, and a vibrating alert.

10. The device for storage and dispensing of a plurality of small objects of claim 1 wherein the counter is an optical sensor.

11. The device for storage and dispensing of a plurality of small objects of claim 1 wherein the outlet of the storage container is downwardly converging.

12. The device for storage and dispensing of a plurality of small objects of claim 1 wherein the connector is transversely moved using a drive motor.

13. The device for storage and dispensing of a plurality of small objects of claim 1 further comprising a wireless link allowing the user to communicate the input signal to the dispensing machine from a remote user input interface, and allowing an output signal to be transmitted from the dispensing machine to the remote user input interface.

14. The device for storage and dispensing of a plurality of small objects of claim 13 wherein the output signal communicates information on the count of the dispensed plurality of small objects, the user access to the storage containers, the user access to the dispersal receptacle and the user access to the error receptacle.

15. A method for storage and dispensing of a plurality of small objects comprising the steps of:
providing a user input interface in electronic communication with a dispensing machine, the dispensing machine comprising:
two adjacent storage-auger devices and a connector, each one of the two storage-auger devices comprising:
a storage container, the storage container defining a substantially hollow interior portion, the hollow interior portion having an inlet and an outlet;
an auger housing defining an interior chamber, the interior chamber being in communication with the storage container outlet;
a rotatable auger disposed within the interior chamber of the auger housing; and
a counter in communication with an outlet of the auger housing;
the connector being directly connected to the sorting receptacle;
adding a plurality of small objects into each one of the two storage containers;
programming a dispersal schedule for the two storage-auger devices using the user input interface, the user input interface communicating the dispersal schedule as an input signal to the dispensing machine;
dispensing at least one of the plurality of small objects from the storage container of one of the two storage-auger devices into the interior chamber of the auger housing based on the programmed dispersal schedule;
propelling the at least one of the plurality of small objects towards the outlet of the auger housing using the rotatable auger;
dispensing the at least one of the plurality of small objects from the outlet of the auger housing into the sorting receptacle;
counting the plurality of small objects dispensed from the outlet of the auger housing using the counter; and
moving the connector from one storage-auger device to the other storage-auger device such that the plurality of small objects dispensed from each one of the storage-auger devices is collected in the sorting receptacle releasing the plurality of small objects within the sorting receptacle into a dispersal chute.

16. The method for storage and dispensing of a plurality of small objects of claim 15 wherein the propelling of plurality of small objects towards the outlet of the auger housing by the rotatable auger uses an actuator system mounted on the connector, an operation of the actuator system comprising the steps of:
engaging an axial shaft to a screw head using a linear actuator, the screw head being embedded on a distal end of the rotatable auger; and
providing a rotary motion of the rotatable auger as the axial shaft engages the screw head using a rotary actuator propelling the plurality of small objects up along the rotatable auger.

17. The method for storage and dispensing of a plurality of small objects of claim 15 further comprising the step of:
alerting a user when a successful count has taken place using an alert mechanism, the successful count being when the plurality of small objects counted by the counter is equal to the plurality of small objects scheduled to be dispensed from the two storage-auger devices according to the dispersal schedule of the input signal from the user input interface, the alert mechanism being at least one of an audio alert, visual alert, and a vibrating alert.

18. A device for storage and dispensing of a plurality of small objects comprising:
a user input interface in electronic communication with a dispensing machine, the user input interface communicating an input signal to the dispensing machine, the input signal providing a count of dispensing a plurality of small objects; and
the dispensing machine comprising:
a storage-auger device and a connector, the storage-auger device comprising:
a storage container, the storage container defining a substantially hollow interior portion, the hollow interior portion having an inlet and an outlet;
an auger housing defining an interior chamber, the interior chamber being in communication with the storage container outlet;
a rotatable auger disposed within the interior chamber of the auger housing constructed and arranged to propel at least one of the plurality of small objects in the interior chamber of the auger housing towards an outlet of the auger housing, wherein the rotatable auger is configured to propel the plurality of small objects towards the outlet of the auger housing using an actuator system mounted on the auger or the connector, the actuator system comprising:
a screw head embedded on a distal end of the rotatable auger;
an axial shaft engageable with the screw head using a linear actuator; and
a rotary actuator propelling the plurality of small objects up along the rotatable auger by providing a rotary motion of the rotatable auger as the axial shaft engages the screw head; and
a counter in communication with the outlet of the auger housing, the counter configured to count at least one of the plurality of small objects being dispensed from the outlet of the auger housing into a sorting receptacle;
the connector being directly coupled to the sorting receptacle.

19. The device for storage and dispensing of a plurality of small objects of claim 1 wherein the sorting receptacle is configured to release the plurality of small objects into a dispersal chute.

20. The method for storage and dispensing of a plurality of small objects of claim 15 wherein the storage container is a vertically oriented storage container, and wherein the outlet is at a bottom lengthwise end of the storage container;
wherein the storage container outlet is at a lengthwise end of the auger housing; and
wherein the counter in communication with the outlet of the auger housing is positioned at an opposite end of the auger housing from the storage container.

* * * * *